(12) United States Patent
Takahashi et al.

(10) Patent No.: US 8,729,332 B2
(45) Date of Patent: May 20, 2014

(54) PANTS-TYPE DISPOSABLE DIAPER

(75) Inventors: Yuki Takahashi, Tsurugi-cho (JP);
Kenji Nakaoka, Osaka (JP)

(73) Assignee: Livedo Corporation, Ehime (JP)

( * ) Notice: Subject to any disclaimer, the term of this patent is extended or adjusted under 35 U.S.C. 154(b) by 278 days.

(21) Appl. No.: 13/321,927

(22) PCT Filed: Mar. 15, 2010

(86) PCT No.: PCT/JP2010/054734
§ 371 (c)(1),
(2), (4) Date: Nov. 22, 2011

(87) PCT Pub. No.: WO2010/137388
PCT Pub. Date: Dec. 2, 2010

(65) Prior Publication Data
US 2012/0083756 A1    Apr. 5, 2012

(30) Foreign Application Priority Data
May 29, 2009  (JP) ................... 2009-130887

(51) Int. Cl.
*A61F 13/15* (2006.01)
*A61F 13/20* (2006.01)

(52) U.S. Cl.
USPC ... 604/365; 604/381; 604/385.29; 604/385.3; 604/393; 604/397; 604/398

(58) Field of Classification Search
USPC ......... 604/365, 381, 385.29, 385.3, 393, 397, 604/398
See application file for complete search history.

(56) References Cited

U.S. PATENT DOCUMENTS 5,928,209 A    7/1999 Bodford et al.

6,132,410 A    10/2000 Van Gompel et al.
(Continued)

FOREIGN PATENT DOCUMENTS

| | | |
|---|---|---|
| EP | 0 248 584 A2 | 12/1987 |
| EP | 0 875 225 A1 | 11/1998 |

(Continued)

OTHER PUBLICATIONS

Translation of JP 2006-247009, Sep. 21, 2006 (JAP).*
Translation of JP 2008-289896, Dec. 4, 2008 (JAP).*
Office Action issued Sep. 12, 2012 in corresponding European Application No. 10 714 489.1.

(Continued)

*Primary Examiner* — Tatyana Zalukaeva
*Assistant Examiner* — Ginger T Chapman
(74) *Attorney, Agent, or Firm* — Wenderoth, Lind & Ponack, L.L.P.

(57) ABSTRACT

A pants-type disposable diaper comprises: a pants-shaped outer member having a front part, a back part, and a crotch part positioned between the front part and the back part, and having a waist opening and a pair of leg openings formed by joining the front part and the back part; an absorbent main body disposed on an inner surface of the pants-shaped outer member at the crotch part, and comprising a top sheet, a back sheet, and an absorbent core disposed between the top sheet and the back sheet; and an end-holding sheet covering a longitudinal end of the absorbent main body at the front part and/or the back part of the pants-shaped outer member, and attached to the pants-shaped outer member and the absorbent main body with a hot-melt adhesive; wherein the end-holding sheet includes a composite nonwoven fabric in which a spunbonded nonwoven fabric layer is laminated on an inner surface of a meltblown nonwonven fabric layer. According to the pants-type disposable diaper on the above, a hot-melt adhesive is prevented from permeating an end-holding sheet, whereby a skin problem is less likely to be caused for the wearer.

4 Claims, 4 Drawing Sheets

(56) References Cited

U.S. PATENT DOCUMENTS

| | | | |
|---|---|---|---|
| 6,635,798 B1 * | 10/2003 | Yoshioka et al. | 604/365 |
| 8,057,456 B2 * | 11/2011 | Shirai et al. | 604/385.29 |
| 8,187,244 B2 * | 5/2012 | Saito | 604/385.31 |
| 8,216,206 B2 * | 7/2012 | Fujioka et al. | 604/385.28 |
| 2007/0043331 A1 * | 2/2007 | Haruki et al. | 604/385.3 |
| 2008/0038982 A1 | 2/2008 | Motomura et al. | |
| 2009/0281512 A1 * | 11/2009 | Saito | 604/365 |
| 2010/0076394 A1 * | 3/2010 | Hayase et al. | 604/385.29 |
| 2010/0222756 A1 * | 9/2010 | Fujioka et al. | 604/365 |

FOREIGN PATENT DOCUMENTS

| | | |
|---|---|---|
| JP | 2006-141549 | 6/2006 |
| JP | 2006-247009 | 9/2006 |
| JP | 2008-142342 | 6/2008 |
| JP | 2008-161525 | 7/2008 |
| JP | 2008-289896 | 12/2008 |
| JP | 2008-295838 | 12/2008 |

OTHER PUBLICATIONS

International Search Report issued Jul. 22, 2010 in corresponding International Application No. PCT/JP2010/054734.
Office Action issued Nov. 26, 2012 in corresponding Australian Application No. 2010253288.
Office Action issued Apr. 3, 2013 in corresponding Chinese Application No. 201080017720.9 (with English translation).
Notice of Reasons for Rejection issued Apr. 30, 2013 in corresponding Japanese Application No. 2009-130887 (with English translation).
Mexican Office Action (with English translation) dated Sep. 11, 2013 issued in corresponding Mexican Application No. MX/a/2011/012499.
Chinese Office Action (with English translation) dated Sep. 26, 2013 issued in corresponding Chinese Application No. 201080017720.9.
Singaporean Office Action mailed Nov. 4, 2013 in corresponding Singaporean Application No. 201108335-9.
Japanese Office Action mailed Jan. 7, 2014 issued in corresponding Japanese Application No. 2009-130887 (with English translation).

* cited by examiner

PANTS-TYPE DISPOSABLE DIAPER

TECHNICAL FIELD

The present invention relates to a pants-type disposable diaper for an infant or an adult.

BACKGROUND ART

Conventionally, there is known a pants-type disposable diaper comprising: a pants-shaped outer member having a front part, a back part, and a crotch part positioned between the front part and the back part; and an absorbent main body provided at the crotch part of the pants-shaped outer member. In the pants-type disposable diaper, a step in a thickness direction of the diaper may be formed between the absorbent main body and the pants-shaped outer member, and a wearer may feel discomfort due to this step. In particular, the wearer is likely to feel discomfort at a longitudinal end of the absorbent main body. In order that the longitudinal end of the absorbent main body is less likely to come into direct contact with a wearer to cause the wearer to feel discomfort, Japanese Laid-Open Patent Publication No. 2006-247009 (Patent Literature 1) discloses that end-holding sheets that cover the longitudinal ends of the absorbent main body are provided at the front part and the back part, respectively, of the pants-shaped outer member. In Patent Literature 1, the end-holding sheets are attached to the pants-shaped outer member and the absorbent main body with a hot-melt adhesive.

CITATION LIST

Patent Literature

Patent Literature 1
Japanese Laid-Open Patent Publication No. 2006-247009

SUMMARY OF INVENTION

Technical Problem

However, the end-holding sheet used in the Patent Literature 1 is made of a spunbonded nonwoven fabric, and therefore, when the end-holding sheet is adhered to the pants-shaped outer member by the hot-melt adhesive, the hot-melt adhesive possibly permeate the end-holding sheet, resulting in causing skin problems for a wearer.

The present invention has been achieved in view of the above circumstances, and an object of the present invention is to provide a pants-type disposable diaper having an end-holding sheet that prevents a hot-melt adhesive from permeating and that is gentle to a skin of a wearer.

Solution to Problem

A pants-type disposable diaper of the present invention which solves the above problems comprises: a pants-shaped outer member having a front part, a back part, and a crotch part positioned between the front part and the back part, and having a waist opening and a pair of leg openings formed by joining the front part and the back part; an absorbent main body disposed on an inner surface of the pants-shaped outer member at the crotch part, and comprising a top sheet, a back sheet, and an absorbent core disposed between the top sheet and the back sheet; and an end-holding sheet covering a longitudinal end of the absorbent main body at the front part and/or the back part of the pants-shaped outer member, and attached to the pants-shaped outer member and the absorbent main body with a hot-melt adhesive; wherein the end-holding sheet includes a composite nonwoven fabric in which a spunbonded nonwoven fabric layer is laminated on an inner surface of a meltblown nonwonven fabric layer.

In the present invention, since the end-holding sheet includes the composite nonwoven fabric in which a spunbonded nonwoven fabric layer is laminated at least on the inner surface of a meltblown nonwoven fabric layer, the hot-melt adhesive used for adhering the end-holding sheet is prevented from permeating by the meltblown nonwoven fabric layer. Therefore, the surface of the end-holding sheet is less likely to become sticky to cause uncomfortable skin feel, and a skin problem is less likely to be caused for the wearer. In addition, since the spunbonded nonwoven fabric layer is laminated on the inner surface of the meltblown nonwoven fabric layer, skin feel of the end-holding sheet against the wearer becomes excellent.

The meltblown nonwonven fabric layer of the composite nonwoven fabric used for the end-holding sheet preferably has a mass per unit area of 1.0 g/m² or more and 3.0 g/m² or less. When the mass per unit area of the meltblown nonwonven fabric layer is within this range, the hot-melt adhesive is certainly prevented from permeating the end-holding sheet, and the end-holding sheet is maintained to be soft, resulting in excellent in skin feel against a wearer.

Preferably, a body elastic member extending in a width direction of the diaper is disposed at the front part and/or the back part of the pants-shaped outer member, and fibers constituting the spunbonded nonwoven fabric layer of the end-holding sheet are oriented in the width direction of the diaper. In this case, the strength of the end-holding sheet in the width direction of the diaper can be enhanced, and as a result, the end-holding sheet is less likely to break even when the body elastic member is provided at the pants-shaped outer member.

Preferably, a body elastic member extending in a width direction of the diaper is disposed at the front part and/or the back part of the pants-shaped outer member, and the end-holding sheet is attached to the pants-shaped outer member and the absorbent main body with a rubber hot-melt adhesive. By using the rubber hot-melt adhesive for adhering the end-holding sheet, the end-holding sheet is less likely to be detached from the pants-shaped outer member even when the pants-shaped outer member and the end-holding sheet are repeatedly stretched and contracted.

The composite nonwoven fabric used for the end-holding sheet is preferably hydrophilized with a surfactant. When the composite nonwoven fabric is hydrophilized with the surfactant, softness of the composite nonwoven fabric increases, and hence skin feel against a wearer becomes excellent.

Advantageous Effects of Invention

In the pants-type disposable diaper of the present invention, a hot-melt adhesive is prevented from permeating an end-holding sheet, whereby a skin problem is less likely to be caused for the wearer. Further, skin feel of the end-holding sheet against the wearer is excellent.

DESCRIPTION OF EMBODIMENTS

Figure 1:
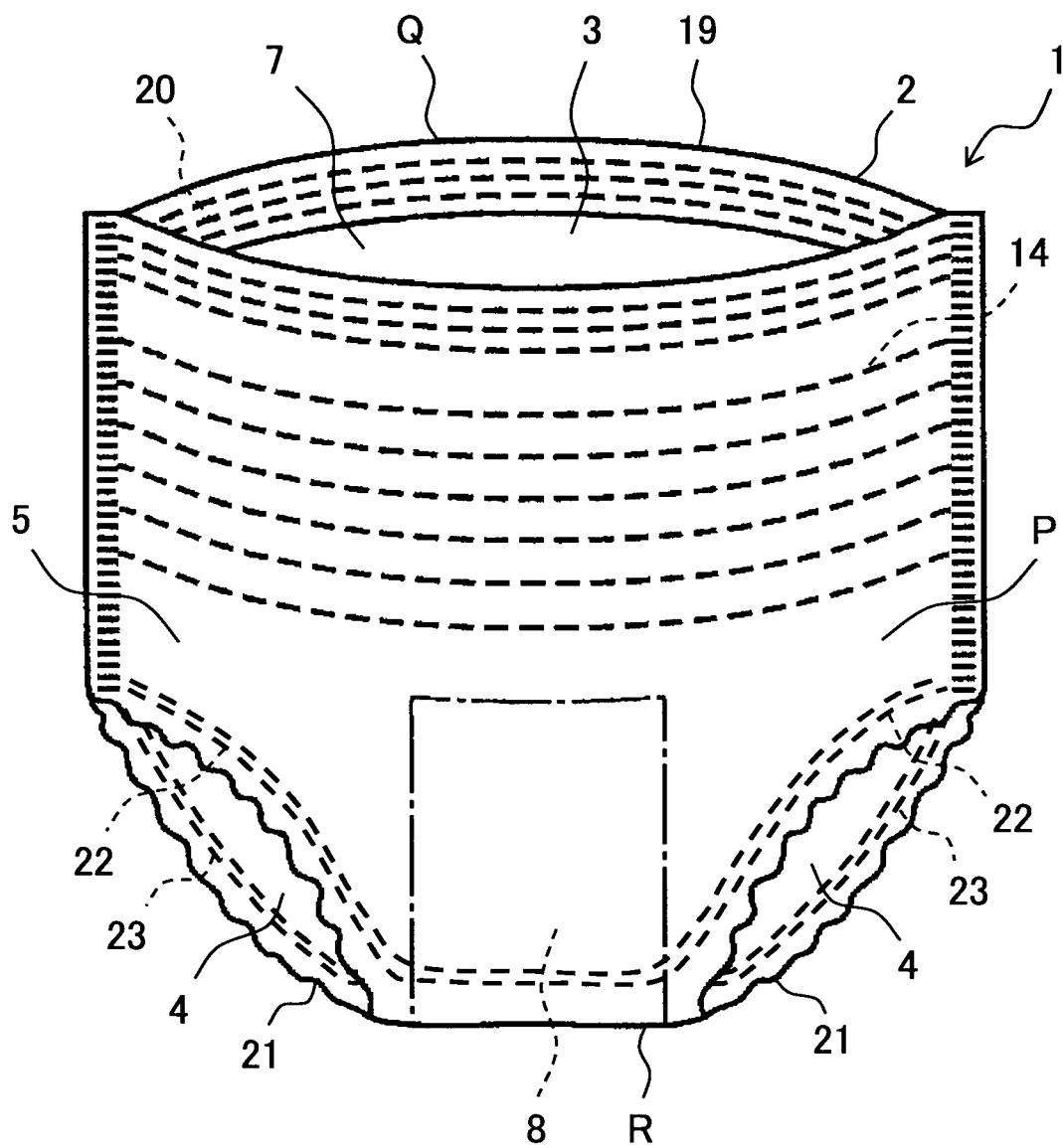
FIG. 1 shows a perspective view of a pants-type disposable diaper of the present invention.

A pants-type disposable diaper of the present invention comprises: a pants-shaped outer member having a front part, a back part, and a crotch part positioned between the front part and the back part, and having a waist opening and a pair of leg openings formed by joining the front part and the back part; and an absorbent main body disposed on an inner surface of the pants-shaped outer member at the crotch part, and comprising a top sheet, a back sheet, and an absorbent core disposed between the top sheet and the back sheet.

In the pants-shaped outer member, the front part and the back part are joined at their both side edges in a width direction of the diaper, whereby forming the pair of leg openings on both sides of the crotch part and the waist opening provided by edges of end parts, with respect to a longitudinal direction of the diaper, of the front part and the back part. Here, the longitudinal direction means a direction from the front part toward the back part of the pants-type disposable diaper. The width direction means a direction orthogonal to the longitudinal direction on the same plane as the pants-type disposable diaper in a state where the front part and the back part of the pants-type disposable diaper are disjoined and the pants-type disposable diaper is developed on a plane.

Concerning names of respective parts of the pants-shaped outer member, a part applied to an abdomen side of a wearer is called the front part, a part applied to a buttocks side of the wearer is called the back part, and a part positioned between the front part and the back part and applied to a crotch of the wearer is called the crotch part, in a state of wearing the pants-type disposable diaper. The crotch part is a middle part when the pants-type disposable diaper is divided into three parts in the longitudinal direction in a state where the front part and the back part of the diaper are disjoined and the diaper is developed on a plane, and the crotch part is a part whose side edges in the width direction are not joined when the diaper is formed in a shape of pants.

The absorbent main body is disposed on the inner surface of the pants-shaped outer member at the crotch part. The inner surface means a surface that faces a wearer's skin in wearing the pants-type disposable diaper. An outer surface means a surface that faces outside in wearing the pants-type disposable diaper. The absorbent main body is disposed at least at the crotch part, and preferably extends to the front part and the back part. The absorbent main body absorbs urine and the like excreted from a wearer.

The pants-shaped outer member may be composed of one sheet that is formed into a predetermined shape, or may be composed of a laminate of two or more sheets that is formed into a predetermined shape. Preferably, the pants-shaped outer member comprises an outer sheet and an inner sheet laminated on an inner surface of the outer sheet. In this case, the inner sheet is preferably formed from a hydrophilic or liquid-impermeable material and more preferably formed from a liquid-impermeable material, and the outer sheet is preferably formed from a liquid-impermeable material. When the pants-shaped outer member is composed of one sheet, the pants-shaped outer member is preferably composed of the outer sheet. When the pants-shaped outer member has a sheet formed from a liquid-impermeable material, leakage of urine and the like from the pants-shaped outer member is prevented.

A nonwoven fabric, a plastic sheet or the like can be used as the inner sheet and the outer sheet. Among them, the inner sheet and the outer sheet are preferably made of a nonwoven fabric.

As a liquid-impermeable nonwoven fabric used for the inner sheet or the outer sheet, a polyolefin nonwoven fabric such as a polyethylene nonwoven fabric, a polypropylene nonwoven fabric and the like, a polyester nonwoven fabric and the like are preferably used, and a polypropylene nonwoven fabric is especially preferably used. By using such a nonwoven fabric, the pants-shaped outer member with high strength can be obtained easily.

When the inner sheet and the outer sheet are made of a nonwoven fabric, a spunbonded nonwoven fabric is preferably used as the nonwoven fabric. When the inner sheet and the outer sheet are made of a spunbonded nonwoven fabric, breathability of the pants-shaped outer member is easily ensured, whereby moisture that is originated from sweat and the like from a wearer is easily released outside. Here, the spunbonded nonwoven fabric means a nonwoven fabric manufactured by a spunbonding method. In the present invention, the spunbonded nonwoven fabric means a nonwoven fabric consisting of a spunbonded layer.

The nonwoven fabric used for the inner sheet and the outer sheet has preferably a mass per unit area of 10 $g/m^2$ or more, more preferably 15 $g/m^2$ or more, preferably 35 $g/m^2$ or less, and more preferably 25 $g/m^2$ or less. When the nonwoven fabric has a mass per unit area of 10 $g/m^2$ or more, the sheet tends to have a sufficient strength. When the nonwoven fabric has a mass per unit area of 35 $g/m^2$ or less, breathability of the nonwoven fabric is easily ensured, resulting in improving a comfort of a wearer.

An end-holding sheet covering a longitudinal end of the absorbent main body is provided at the front part and/or the back part of the pants-shaped outer member. When the end-holding sheet is provided, a wearer is less likely to feel discomfort that is caused by the longitudinal end of the absorbent main body coming into direct contact with a skin of the wearer. The end-holding sheet is preferably provided at both the front part and the back part of the pants-shaped outer member.

The end-holding sheet is provided astride the absorbent main body and the pants-shaped outer member so as to cover the longitudinal end of the absorbent main body in the longitudinal direction of the diaper. The end-holding sheet only needs to be provided at least at the front part and/or the back part. For example, when the absorbent main body is placed only at the crotch part, the end-holding sheet may be provided so as to extend from the front part to the crotch part or from the back part to the crotch part. However, preferably, the absorbent main body is provided so as to extend from the crotch part to the front part and the back part, and the end-holding sheet is provided only at the front part and/or the back part. The end-holding sheet may be provided to the entirety of the front part and/or the back part, or may be provided to a part of the front part and/or the back part.

The end-holding sheet is provided so as to extend across the absorbent main body in the width direction of the diaper. Preferably, the end-holding sheet is provided so as to coincide with the pants-shaped outer member in the width direction of the diaper. When the end-holding sheet is provided so as to coincide with the pants-shaped outer member in the width direction of the diaper, the end-holding sheet is easily provided to the pants-type disposable diaper when continuously producing the pants-type disposable diaper.

The end-holding sheet is attached to the pants-shaped outer member and the absorbent main body with a hot-melt adhesive. Specifically, the end-holding sheet is attached to the front part and/or the back part of the pants-shaped outer member and the longitudinal end of the absorbent main body with the hot-melt adhesive. By using the hot-melt adhesive, even when a step is formed between the pants-shaped outer member and the longitudinal end of the absorbent main body, the end-holding sheet can be reliably attached to both of the members.

The end-holding sheet is provided so as to face a skin of a wearer and covers the longitudinal end of the absorbent main body where unevenness is particularly great. As a result, during wearing of the diaper, the end-holding sheet comes into direct contact with the skin of the wearer strongly. Therefore, in order to provide an excellent skin feel against the wearer, a surface of the end-holding sheet which faces the skin of the wearer is made from a spunbonded nonwoven fabric layer. However, in the spunbonded nonwoven fabric layer, voids among fibers constituting the nonwoven fabric tend to be large. Thus, when the end-holding sheet consists of a spunbonded nonwoven fabric layer, a hot-melt adhesive used for adhering the end-holding sheet possibly permeate the end-holding sheet, and hence the surface of the end-holding sheet may become sticky to cause uncomfortable skin feel and skin problems may be caused for the wearer.

For that reason, in the present invention, a composite nonwoven fabric in which a spunbonded nonwoven fabric layer is laminated at least on an inner surface of a meltblown nonwoven fabric layer is used for the end-holding sheet. In the meltblown nonwoven fabric layer, voids among fibers constituting the nonwoven fabric are small, and hence, when the end-holding sheet has the meltblown nonwoven fabric layer, a hot-melt adhesive is prevented from permeating the end-holding sheet. In addition, skin feel of the end-holding sheet against the wearer becomes excellent, because the spunbonded nonwoven fabric layer is laminated on the inner surface of the meltblown nonwoven fabric layer.

The meltblown nonwoven fabric layer of the composite nonwoven fabric used for the end-holding sheet has preferably a mass per unit area of $1.0 \text{ g/m}^2$ or more, more preferably $1.5 \text{ g/m}^2$ or more, preferably $3.0 \text{ g/m}^2$ or less, and more preferably $2.5 \text{ g/m}^2$ or less. When the meltblown nonwoven fabric layer has a mass per unit area of $1.0 \text{ g/m}^2$ or more, a hot-melt adhesive is certainly prevented from permeating the end-holding sheet. When the meltblown nonwoven fabric layer has a mass per unit area of $3.0 \text{ g/m}^2$ or less, stiffness of the end-holding sheet is not enhanced excessively, whereby the end-holding sheet is maintained to be soft and is excellent in skin feel against a wearer.

As the end-holding sheet, the composite nonwoven fabric in which a spunbonded nonwoven fabric layer is laminated at least on the inner surface of a meltblown nonwoven fabric layer is used, and the composite nonwoven fabric in which spunbonded nonwoven fabric layers are laminated on the inner and outer surfaces, respectively, of a meltblown nonwoven fabric layer may be used, for example. Examples of such a nonwoven fabric include an SMS nonwoven fabric and an SMMS nonwoven fabric. When a meltblown nonwoven fabric layer is interposed between spunbonded nonwoven fabric layers, strength of the end-holding sheet can be enhanced.

The composite nonwoven fabric used for the end-holding sheet has preferably a mass per unit area of $5.0 \text{ g/m}^2$ or more, more preferably $7.5 \text{ g/m}^2$ or more, preferably $25.0 \text{ g/m}^2$ or less, and more preferably $15.0 \text{ g/m}^2$ or less. Since the end-holding sheet is provided so as to overlap the pants-shaped outer member, the composite nonwoven fabric having an excess mass per unit area may provide bulky and rough feel against a wearer. Therefore, in order that, during wearing of the diaper, the bulky and rough feel is not provided at a part where the end-holding sheet is provided, the mass per unit area of the composite nonwoven fabric is preferably lower as long as strength of the end-holding sheet is ensured. In order to achieve both desired strength and thickness, the composite nonwoven fabric used for the end-holding sheet is preferably has a mass per unit area of $5.0 \text{ g/m}^2$ or more and $25.0 \text{ g/m}^2$ or less.

The composite nonwoven fabric of the end-holding sheet is preferably hydrophilized with a surfactant. When the composite nonwoven fabric is hydrophilized with the surfactant, softness of the composite nonwoven fabric increases, and hence skin feel against a wearer becomes excellent. In order to hydrophilize the composite nonwoven fabric with the surfactant, the composite nonwoven fabric may be immersed in a surfactant; a surfactant may be applied to the composite nonwoven fabric; a surfactant may be applied to fibers for constituting the composite nonwoven fabric or the fibers may be immersed in a surfactant and the composite nonwoven fabric may be formed from the fibers; or a hydrophilic component may be mixed with fibers and the composite nonwoven fabric may be formed from the fibers.

A body elastic member extending in the width direction of the diaper is preferably disposed at the front part and/or the back part of the pants-shaped outer member. The body elastic member improves a fitting property of the diaper around abdomen and hip regions. The body elastic member is provided so as to overlap the end-holding sheet or so as to be adjacent to the end-holding sheet. Thus, when the body elastic member is provided at the pants-shaped outer member, the end-holding sheet is greatly affected by a contractive force of the body elastic member. As a result, during wearing the diaper, the end-holding sheet is repeatedly stretched and contracted in the width direction of the diaper. In this case, the end-holding sheet may be detached from the pants-shaped outer member or the end-holding sheet may break.

Therefore, when the body elastic member is provided at the pants-shaped outer member, a rubber hot-melt adhesive is preferably used as the hot-melt adhesive for attaching the end-holding sheet to the pants-shaped outer member and the absorbent main body. By using the rubber hot-melt adhesive, the end-holding sheet is less likely to be detached from the pants-shaped outer member, even when the pants-shaped outer member and the end-holding sheet are repeatedly stretched and contracted. The rubber hot-melt adhesive is not particularly limited as long as it exhibits rubber elasticity, and styrene elastomers such as styrene-isoprene-styrene block copolymers (SIS), styrene-butadiene-styrene block copolymers (SBS), styrene-ethylene-butadiene-styrene block copolymers (SEBS), and styrene-ethylene-propylene-styrene block copolymers (SEPS) are preferably used. These exemplified styrene elastomers may be used either alone or as a combination of at least two of them.

The rubber hot-melt adhesive may further contain a tackifier, an antioxidant, a plasticizer, a softener, a viscosity modifier, or the like in addition to the styrene elastomer. As the tackifier, a conventionally known tackifier may be used, and examples of the tackifier include dicyclopentadiene resins, C5 or C9 hydrocarbon resins, alicyclic hydrocarbon resins, rosins, terpenes, and the like. In light of ensuring sufficient adhesion and flexibility, the rubber hot-melt adhesive preferably contains the styrene elastomer in an amount of 10 mass % to 40 mass % (more preferably 15 mass % to 30 mass %), and preferably contains the tackifier in an amount of 30 mass % to 70 mass % (more preferably 40 mass % to 60 mass %). These proportions are adjusted arbitrarily in the range where the sum of the proportions of all components does not exceed 100 mass %.

When the body elastic member is provided at the pants-shaped outer member, fibers constituting the spunbonded nonwoven fabric layer of the end-holding sheet are preferably oriented in the width direction of the diaper, in order for the end-holding sheet to be resistant to stretching and contracting in the width direction of the diaper. As explained above, thickness of the composite nonwoven fabric that constitutes the end-holding sheet is preferably thinner. When the fibers constituting the spunbonded nonwoven fabric layer of the composite nonwoven fabric are oriented in the width direction of the diaper, the strength of the end-holding sheet in the width direction of the diaper can be enhanced even though a mass per unit area of the composite nonwoven fabric is not increased. As a result, even when the body elastic member is provided at the pants-shaped outer member, the end-holding sheet is less likely to break in spite of thickness thereof to be thin. In particular, in wearing or removing the diaper, the end-holding sheet is less likely to break even when the diaper is pulled in the width direction thereof in order to expand the waist opening.

The orientation of the fibers constituting the spunbonded nonwoven fabric layer will be described as follows. The spunbonded nonwoven fabric is obtained, for example, by: melting a polymer material; extruding the melted polymer material from a spinning nozzle to be extended; collecting the extended polymer material on a conveyor belt or the like to be formed into a web shape. On this occasion, the webs (fibers) collected on the conveyor belt are arranged along a moving direction of the conveyor belt. Thus, in this case, the webs (fibers) are oriented along the moving direction (MD direction) of the conveyor belt. The orientation direction of the fibers of the spunbonded nonwoven fabric layer can be recognized by observing a surface of the spunbonded nonwoven fabric layer with a microscope or the like.

The pants-shaped outer member may further comprise a waist elastic member or a leg elastic member, preferably. The waist elastic member is disposed along a waist opening edge and prevents excrement such as urine and the like from leaking from a back side or an abdomen side, even when a wearer lies. The leg elastic member is disposed along a leg opening edge and prevents excrement such as urine and the like from leaking from the leg opening edge. Here, the waist opening edge means an edge of the waist opening in the pants-shaped outer member, and the leg opening edge means an edge of the leg opening in the pants-shaped outer member.

When the pants-shaped outer member is composed of one sheet, the respective elastic members are fixed on the sheet by means of a hot-melt adhesive or the like. When the pants-shaped outer member is composed of the inner sheet and the outer sheet, the respective elastic members are disposed between the both sheets and are fixed to the inner sheet and/or the outer sheet by means of a hot-melt adhesive or the like, preferably. Each of the elastic members may be composed of a plurality of elastic members.

Elastic materials such as a polyurethane thread, a polyurethane film, a natural rubber and the like, which are generally used for disposable diapers, can be used for respective elastic members. The respective elastic members are preferably fixed in a stretched state with a hot-melt adhesive. For example, a polyurethane thread having a fineness of 100 dtex to 2,500 dtex is stretched at a ratio of 1.1 to 5.0 times to be fixed. A preferable bonding means is a rubber hot-melt adhesive.

The absorbent main body disposed on the inner surface of the pants-shaped outer member at the crotch part comprises a top sheet, a back sheet, and an absorbent core disposed between the top sheet and the back sheet. The top sheet is preferably made of a liquid-permeable nonwoven fabric or the like, and the back sheet is preferably made of a nonwoven fabric, a plastic film or the like which is liquid-impermeable or water-repellent.

The absorbent core is not particularly limited as long as it absorbs excrement such as urine and the like; however, it preferably contains an absorbent resin. The absorbent core can be obtained, for example, by the steps of mixing a granular absorbent resin with a hydrophilic fiber assembly such as crushed pulp fibers, cellulose fibers and the like to obtain a clump, or dispersing the granular absorbent resin to the hydrophilic fiber assembly to obtain a clump; wrapping the clump with a paper sheet such as a tissue paper and the like, or with a cover sheet such as a liquid-permeable nonwoven fabric sheet and the like; and molding the obtained wrapped clump into a predefined shape such as a rectangular shape, an hourglass shape, a center nipped-in gourd shape, a battledore shape, and the like.

Rising flaps are preferably provided along edges of opposite side, with respect to the width direction, of the absorbent main body. For example, the rising flaps may be joined to the top sheet of the absorbent main body, or may be provided outside the absorbent main body in the width direction. The rising flaps are preferably made of a nonwoven fabric, a plastic film or the like which is liquid-impermeable or water-repellent, and more preferably made of a water-repellent nonwoven fabric. Providing the rising flaps enables to prevent lateral leakage of urine and the like.

A rising elastic member is preferably disposed at an upper end (an end nearer to a wearer) of the rising flap being in a rising state. The rising flap forms a rising gather which rises toward a wearer due to a shrinkage force of the rising elastic member, thereby preventing lateral leakage of urine and the like. An inner surface of the rising flap may be joined to the top sheet at ends, with respect to the longitudinal direction of the diaper, of the rising flaps, thereby preventing leakage of urine and the like in the longitudinal direction.

Next, an example of the pants-type disposable diaper of the present invention is explained, referring to drawings. However, the present invention is not restricted to the following embodiment.

Figure 2:
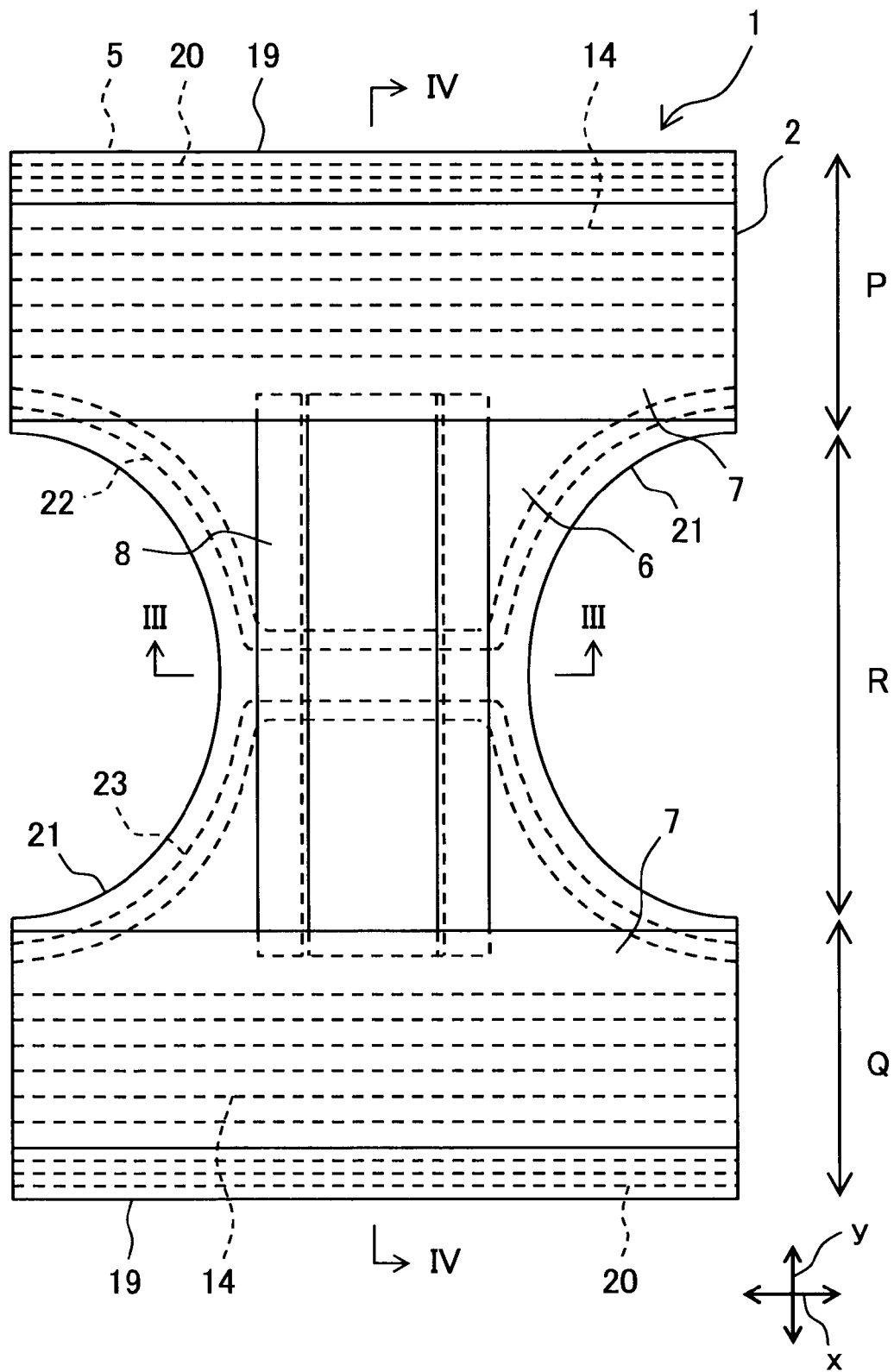
FIG. 2 shows a plan view of the pants-type disposable diaper shown in FIG. 1 in a developed state in which a front part and a back part are disjoined.
Figure 3:
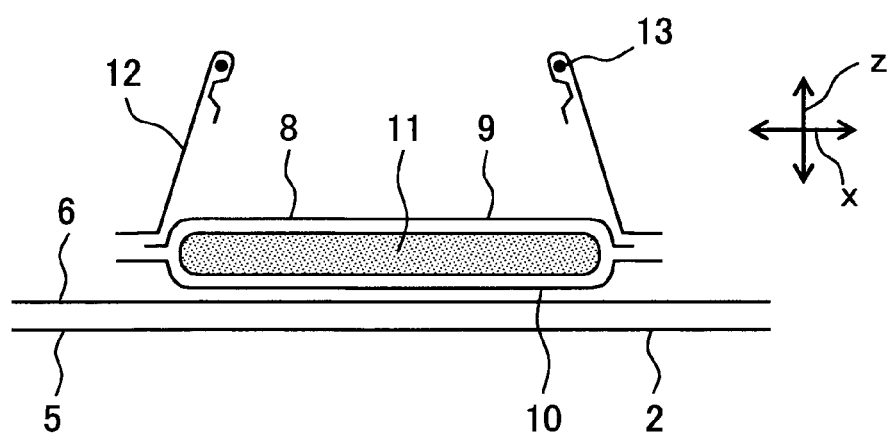
FIG. 3 shows a cross-sectional view taken along line III-III in FIG. 2.
Figure 4:
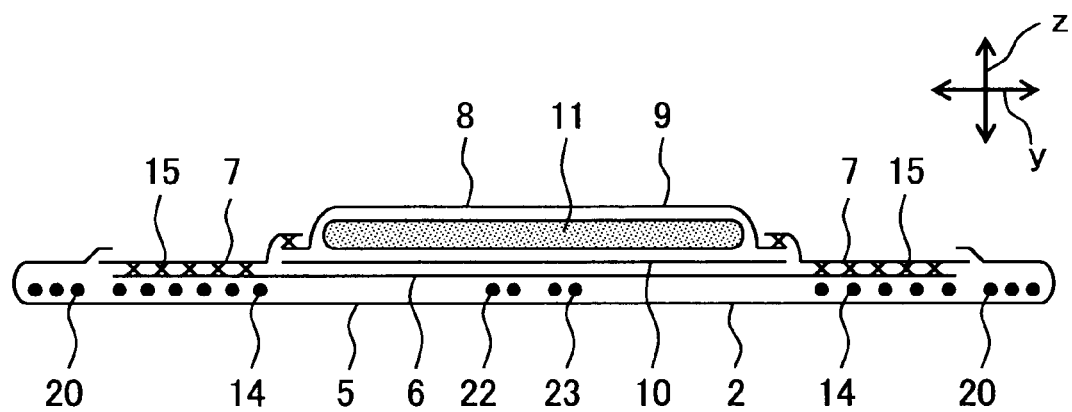
FIG. 4 shows a cross-sectional view taken along line IV-IV in FIG. 2.

FIG. 1 shows a perspective view of a pants-type disposable diaper of the present invention. FIG. 2 shows a plan view of the pants-type disposable diaper shown in FIG. 1 in a developed state in which a front part and a back part are disjoined. FIG. 3 shows a cross-sectional view taken along line III-III in FIG. 2. FIG. 4 shows a cross-sectional view taken along line IV-IV in FIG. 2. In the drawings, the arrow x direction is defined as a width direction of the diaper, and the arrow y is defined as a longitudinal direction of the diaper. The direction perpendicular to the plane formed by the arrows x and y is defined as a thickness direction z.

A pants-type disposable diaper 1 comprises a pants-shaped outer member 2 having a front part P, a back part Q, and a crotch part R positioned between the front part P and the back part Q, and having a waist opening 3 and a pair of leg openings 4 formed by joining the front part P and the back part Q. The pants-shaped outer member 2 comprises an outer sheet 5 and an inner sheet 6 laminated on an inner surface of the outer sheet 5.

The pants-type disposable diaper 1 further comprises an absorbent main body 8 disposed on an inner surface of the pants-shaped outer member 2 at the crotch part R, and comprising a top sheet 9, a back sheet 10, and an absorbent core 11 disposed between the top sheet 9 and the back sheet 10 (FIG. 3). The top sheet 9 is placed so as to face a wearer's skin, and allows excrement such as urine and the like to permeate through. The excrement that permeated the top sheet 9 is accommodated in the absorbent core 11. The back sheet 10 is attached to the inner sheet 6 of the pants-shaped outer member 2, and prevents the excrement from leaking outside.

Rising flaps 12 are provided along an edge of opposite sides, with respect to the width direction x, of the absorbent main body 8. The rising flap 12, which extends in the longitudinal direction y of the diaper, is joined astride the top sheet 9 and the back sheet 10. A rising elastic member 13 is disposed at an inner end in the width direction x of the rising flap 12. A rising gather which rises upward (toward a wearer) is formed from the rising flap 12 due to a shrinkage force of the rising elastic member 13, thereby preventing lateral leakage of urine and the like. An inner surface of the rising flaps 12 is joined to the top sheet 9 at longitudinal ends of the absorbent main body 8, thereby preventing leakage of urine and the like outward in the longitudinal direction y.

A plurality of body elastic members 14 are disposed between the outer sheet 5 and the inner sheet 6 at the front part P and the back part Q of the pants-shaped outer member 2 so as to extend in the width direction x of the diaper. The body elastic member 14 is fixed to the outer sheet 5 and the inner sheet 6 with a hot-melt adhesive.

As shown in FIGS. 2 and 4, an end-holding sheet 7 is provided so as to cover the longitudinal end of the absorbent main body 8 at the front part P and the back part Q of the pants-shaped outer member 2, and the end-holding sheet 7 is attached to the pants-shaped outer member 2 and the absorbent main body 8 with a hot-melt adhesive 15. In the drawings, the end-holding sheet 7 is provided on the pants-shaped outer member 2 so as to cover the entirety of the body elastic members 14.

Figure 5A:
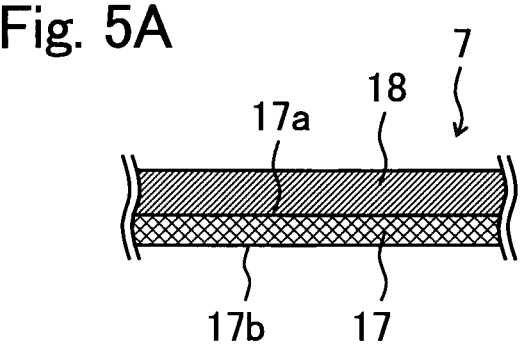
FIGS. 5A and 5B show examples of a composite nonwoven fabric used for an end-holding sheet.
Figure 5B:
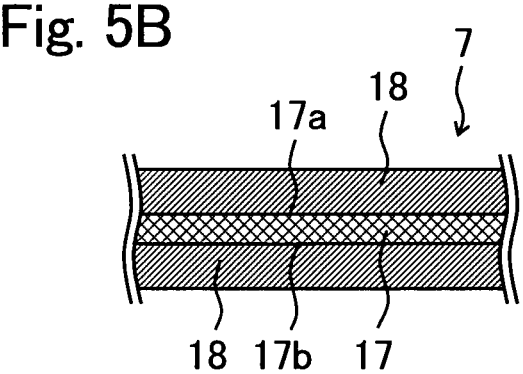

FIGS. 5A and 5B show examples of a composite nonwoven fabric that forms the end-holding sheet 7. In FIG. 5A, the end-holding sheet 7 is composed of a composite nonwoven fabric in which a spunbonded nonwoven fabric layer 18 is laminated on an inner surface 17a of a meltblown nonwoven fabric layer 17. In FIG. 5B, the end-holding sheet 7 is composed of a composite nonwoven fabric in which spunbonded nonwoven fabric layers 18 are laminated on an inner surface 17a and an outer surface 17b, respectively, of a meltblown nonwoven fabric layer 17.

A plurality of waist elastic members 20 extending in the width direction x of the diaper is disposed along a waist opening edge 19, which is an edge of the waist opening 3, of the pants-shaped outer member 2. The outer sheet 5 is folded back at the waist opening edge 19 of the pants-shaped outer member 2 toward the inner sheet 6, and the folded outer sheet 5 is adhered to the end-holding sheet 7 with a hot-melt adhesive. The waist elastic members 20 are interposed between the folded and unfolded parts of the outer sheet 5 and adhered to the outer sheet 5.

Leg elastic members 22 and 23 are disposed between the outer sheet 5 and the inner sheet 6 along the leg opening edges 21, which is edges of the leg openings 4, of the pants-shaped outer member 2. The leg elastic member consists of: a front leg elastic member 22 provided so as to extend across the crotch part R and along the leg opening edges on a front side of the diaper; and a back leg elastic member 23 provided so as to extend across the crotch part R and along the leg opening edges on a back side of the diaper. By the front leg elastic member 22 and the back leg elastic member 23, the leg elastic member is provided along substantially the entire circumference of the leg opening edges 21.

REFERENCE SIGNS LIST

1: a pants-type disposable diaper
2: a pants-shaped outer member
5: an outer sheet
6: an inner sheet
7: an end-holding sheet
8: an absorbent main body
9: a top sheet
10: a back sheet
11: an absorbent core
14: a body elastic member
15: a hot-melt adhesive

The invention claimed is:

1. A pants-type disposable diaper comprising:
a pants-shaped outer member having a front part, a back part, and a crotch part positioned between the front part and the back part, and having a waist opening and a pair of leg openings formed by joining the front part and the back part;
a body elastic member extending in a width direction of the diaper, the body elastic member being disposed at the front part or the back part of the pants-shaped outer member;
an absorbent main body disposed on an inner surface of the pants-shaped outer member at the crotch part, and comprising a top sheet, a back sheet, and an absorbent core disposed between the top sheet and the back sheet; and
an end-holding sheet covering a longitudinal end of the absorbent main body at the front part or the back part of the pants-shaped outer member, and attached to the pants-shaped outer member and the absorbent main body with a hot-melt adhesive, wherein
the end-holding sheet includes a composite nonwoven fabric in which a spunbonded nonwoven fabric layer is laminated on an inner surface of a meltblown nonwonven fabric layer, and wherein fibers constituting the spunbonded nonwoven fabric layer of the end-holding sheet are oriented in the width direction of the diaper.

2. The pants-type disposable diaper according to claim 1, wherein the meltblown nonwonven fabric layer of the composite nonwoven fabric has a mass per unit area of 1.0 g/m² or more and 3.0 g/m² or less.

3. The pants-type disposable diaper according to claim 1, wherein
the hot-melt adhesive is a rubber hot-melt adhesive.

4. The pants-type disposable diaper according to claim 1, wherein the composite nonwoven fabric is hydrophilized with a surfactant.

* * * * *